United States Patent
Hughes et al.

(10) Patent No.: US 11,634,745 B2
(45) Date of Patent: *Apr. 25, 2023

(54) SYSTEMS AND METHODS FOR SAMPLE PREPARATION FOR ENZYMATIC A1C DETECTION AND QUANTIFICATION

(71) Applicant: POLYMER TECHNOLOGY SYSTEMS, INC., Indianapolis, IN (US)

(72) Inventors: Gary Hughes, Camby, IN (US); Brittney Werner, Fairland, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 290 days.

This patent is subject to a terminal disclaimer.

(21) Appl. No.: 15/839,550

(22) Filed: Dec. 12, 2017

(65) Prior Publication Data

US 2018/0251811 A1 Sep. 6, 2018

Related U.S. Application Data

(60) Provisional application No. 62/466,983, filed on Mar. 3, 2017.

(51) Int. Cl.
| | | |
|---|---|---|
| *C12Q 1/37* | (2006.01) | |
| *C12Q 1/00* | (2006.01) | |
| *G01N 33/72* | (2006.01) | |
| *G01N 33/558* | (2006.01) | |
| *G01N 1/28* | (2006.01) | |

(52) U.S. Cl.
CPC .............. *C12Q 1/37* (2013.01); *C12Q 1/004* (2013.01); *C12Q 1/005* (2013.01); *G01N 1/28* (2013.01); *G01N 33/558* (2013.01); *G01N 33/723* (2013.01); *G01N 2333/90677* (2013.01); *G01N 2333/96486* (2013.01)

(58) Field of Classification Search
None
See application file for complete search history.

(56) References Cited

U.S. PATENT DOCUMENTS

| | | | |
|---|---|---|---|
| 5,695,949 A | 12/1997 | Galen et al. | |
| 10,670,615 B2* | 6/2020 | Xie | G01N 33/726 |
| 2004/0265941 A1 | 12/2004 | Galen et al. | |
| 2006/0030050 A1* | 2/2006 | Milne | G01N 33/54313 436/67 |
| 2010/0025264 A1* | 2/2010 | Yuan | C12Q 1/005 205/777.5 |
| 2011/0005941 A1* | 1/2011 | Blythe | G01N 27/3273 205/777.5 |
| 2011/0269147 A1 | 11/2011 | Chinnayelka | |
| 2012/0208226 A1 | 8/2012 | Ikebukuro et al. | |
| 2012/0296189 A1 | 11/2012 | Bhogal et al. | |
| 2013/0171028 A1 | 7/2013 | Shaffer et al. | |
| 2013/0171676 A1* | 7/2013 | Murakami | C12Q 1/26 435/23 |
| 2014/0273187 A1 | 9/2014 | Johnson et al. | |
| 2014/0370539 A1 | 12/2014 | Shen et al. | |

FOREIGN PATENT DOCUMENTS

| | | | |
|---|---|---|---|
| CN | 1215168 A | 4/1999 | |
| CN | 1244259 A | 2/2000 | |
| CN | 101236192 A | 8/2008 | |
| CN | 102076867 A | 5/2011 | |
| CN | 103124793 A | 5/2013 | |
| CN | 105163661 A | 12/2015 | |
| EP | 2604698 A1 | 6/2013 | |
| JP | 2008245657 A | 10/2008 | |
| KR | 101541798 B1 | 8/2015 | |
| WO | WO-2007094354 A1 * | 8/2007 | ............. C12Q 1/005 |
| WO | WO2009140343 A1 | 11/2009 | |
| WO | WO2015060429 A1 | 4/2015 | |

OTHER PUBLICATIONS

International Search Report and Written Opinion dated Oct. 30, 2017 issued in related PCT App. No. PCT/US2017/045716 (14 pages).
International Search Report and Written Opinion dated Feb. 12, 2018 issued in related PCT App. No. PCT/US2017/065874 (8 pages).
Suh et al., "Remarkable Proteolytic Activity of Imidazoles Attached to Cross-Linked Polystyrene," The Journal of Organic Chemistry, vol. 65, No. 22, Sep. 29, 2000 [retrieved on Jan. 26, 2018]. Retrieved from the Interent: <URL: http://pubs.acs.org/doi/abs/10.1021/jo000896q>.
Office Action dated Sep. 29, 2021 issued in related India patent application No. 201937039691 (6 pages).
Extended European Search Report dated Oct. 4, 2021 issued in related European patent application No. 17934977.4 (5 pages).
Office Action dated Feb. 24, 2022 issued in related India patent application No. 201937039649 (6 pages).
Office Action dated May 18, 2022 issued in related Chinese patent application No. 201780089687.2 (16 pages with translation).
Office Action dated Nov. 7, 2022 issued in Chinese patent application No. 201780089613.9 (23 pages).

\* cited by examiner

*Primary Examiner* — Nghi V Nguyen
(74) *Attorney, Agent, or Firm* — Haynes and Boone, LLP

(57) ABSTRACT

A system for preparing a sample containing hemoglobin HbA1c for measurement by an electrochemical sensor includes a lysing formulary, the lysing formulary including a zwitterionic surfactant. The system further includes a oxidizing formulary, the oxidizing formulary including a cationic surfactant and a isothiazoline derivative and a protease formulary, the protease formulary including a molecule including an azole.

6 Claims, 5 Drawing Sheets

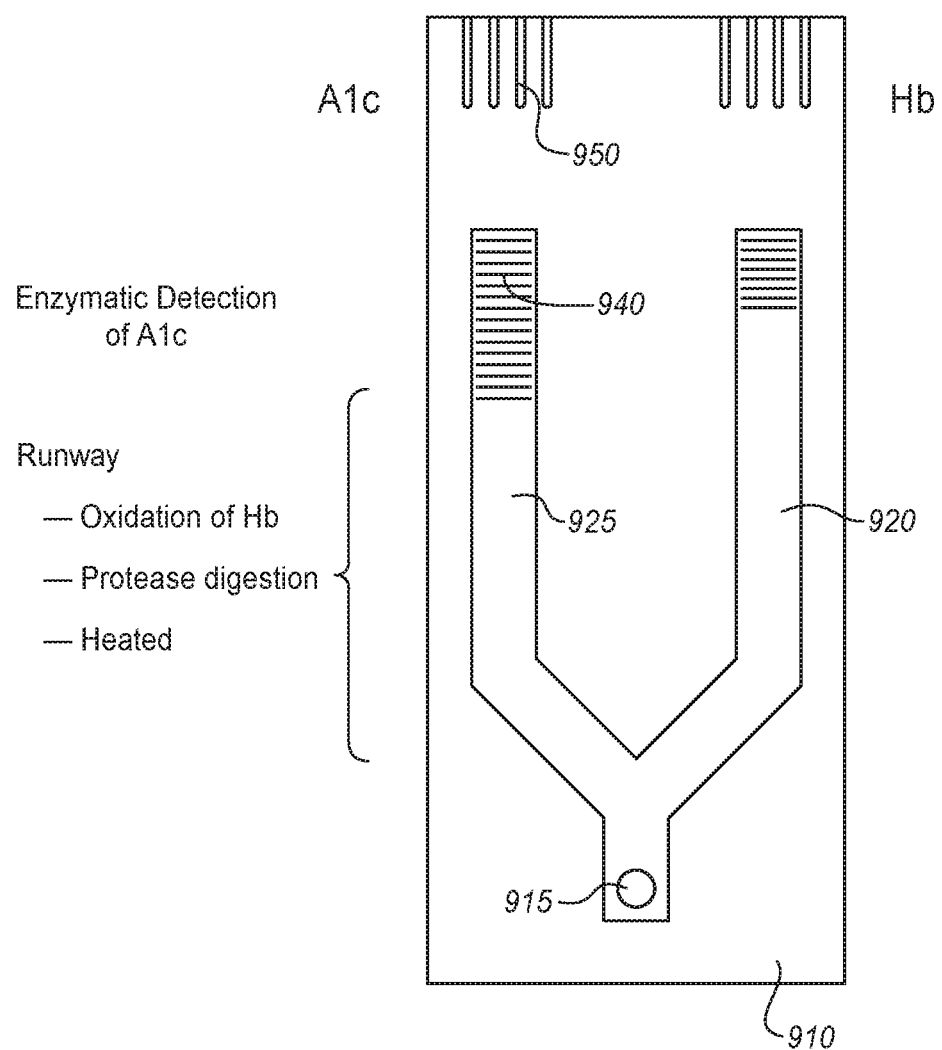

SYSTEMS AND METHODS FOR SAMPLE PREPARATION FOR ENZYMATIC A1C DETECTION AND QUANTIFICATION

CROSS-REFERENCE TO RELATED APPLICATION

This application claims the benefit of U.S. Provisional Application No. 62/466,983 filed on Mar. 3, 2017, which is incorporated herein by reference in its entirety.

BACKGROUND

Point of Care ("POC") and home testing for various blood analytes and other detectable metrics in bodily fluids is desirable for patient and doctor. One such analyte is A1C, a type of glycated hemoglobin. High levels of blood glucose cause over-glycation of proteins, including hemoglobin, throughout the body. Glycation of hemoglobin occurs primarily at the amino termini of beta chains, as well as other sites with free amino groups. Hemoglobin A undergoes a slow glycation with glucose that is dependent on the time-average concentration of glucose over the 120-day life span of red blood cells. The most prevalent and well-characterized species of glycated hemoglobin A is A1C, making up approximately 3% to 6% of the total hemoglobin in healthy individuals. The correlation of A1C and blood glucose levels make it a useful method for monitoring long-term blood glucose levels in people with diabetes. The mean (average) blood glucose level (MBG) is a function of the A1C levels, and is therefore derivable.

BRIEF SUMMARY

In one embodiment, a system for preparing a sample containing hemoglobin A1c for measurement by an electrochemical sensor includes a lysing formulary, the lysing formulary including a zwitterionic surfactant. The system further includes an oxidizing formulary, the oxidizing formulary including a cationic surfactant and an isothiazoline derivative and a protease formulary, the protease formulary including a molecule including an azole. In alternative embodiments the zwitterionic surfactant may be another surfactant. In one alternative, the zwitterionic surfactant is n-Tetradecyl-N,N-dimethyl-3-ammonio-1-propanesulfonate (Zwittergent 3-14®). In another alternative, the cationic surfactant is 1-Dodecyl pyridinium chloride and the isothiazoline derivative is 1,2 Benzisothiazol-3(2H)-one. Alternatively, the protease formulary includes Neutral Proteinase. In one alternative, the azole is imidazole. Optionally, the imidazole is 1M at a pH of 7.5. Alternatively, the system includes a sampler/mixer device, and the lysing formulary is located in the sampler/mixer device. In another alternative, the system includes a test strip and the oxidizing formulary and protease formulary are located in the test strip.

In one embodiment, a system for determining a percent glycation of hemoglobin as HbA1C includes a first electrochemical test area, the first electrochemical test area providing for an HbA1C concentration; and a second electrochemical test area, the second electrochemical test area providing for the total amount of hemoglobin. The system further includes a lysing formulary, the lysing formulary including a zwitterionic surfactant. The system further includes an oxidizing formulary, the oxidizing formulary including a cationic surfactant and a isothiazoline derivative and a protease formulary, the protease formulary including a molecule including an azole. In one alternative, the first electrochemical test area includes a strip with a coating of Fructosyl Amino acid oxidase or fructosyl peptide oxidase. In another alternative, the first electrochemical test area includes ruthenium hexamine trichloride mediator. In yet another alternative, the first electrochemical test area includes a ferricyanide mediator. Alternatively, the zwitterionic surfactant is n-Tetradecyl-N,N-dimethyl-3-ammonio-1-propanesulfonate (Zwittergent 3-14®). In another alternative, the cationic surfactant is 1-Dodecyl pyridinium chloride and the isothiazoline derivative is 1,2 Benzisothiazol-3(2H)-one. Alternatively, the protease formulary includes Neutral Proteinase. In one alternative, the azole is imidazole. Optionally, the imidazole is 1M at a pH of 7.5. In one alternative, the imidazole is between 0.5 to 2M. In another alternative, a pH of the imidazole is between 6-8. Alternatively, the system includes a sampler/mixer device, and the lysing formulary is located in the sampler/mixer device. In another alternative, the system includes a test strip and the oxidizing formulary and protease formulary are located in the test strip.

In one embodiment, a method of preparing a sample for electrochemical hemoglobin A1C determination includes receiving a blood sample. The method further includes lysing red blood cells in the blood sample with a lysing formulary, the lysing formulary including a zwitterionic surfactant. The method further includes oxidizing hemoglobin in the blood sample an oxidizing formulary, the oxidizing formulary including a cationic surfactant and a isothiazoline derivative. The method further includes digesting hemoglobin with a protease formulary, the protease formulary including a molecule including an azole. In one alternative, the zwitterionic surfactant is n-Tetradecyl-N,N-dimethyl-3-ammonio-1-propanesulfonate (Zwittergent 3-14®). In another alternative, the cationic surfactant is 1-Dodecyl pyridinium chloride and the isothiazoline derivative is 1,2 Benzisothiazol-3(2H)-one. Alternatively, the protease formulary includes Neutral Proteinase. In one alternative, the azole is imidazole.

BRIEF DESCRIPTION OF THE DRAWINGS

FIG. 9 shows one embodiment of an electrochemical strip for HbA1c.

DETAILED DESCRIPTION

Figure 1:
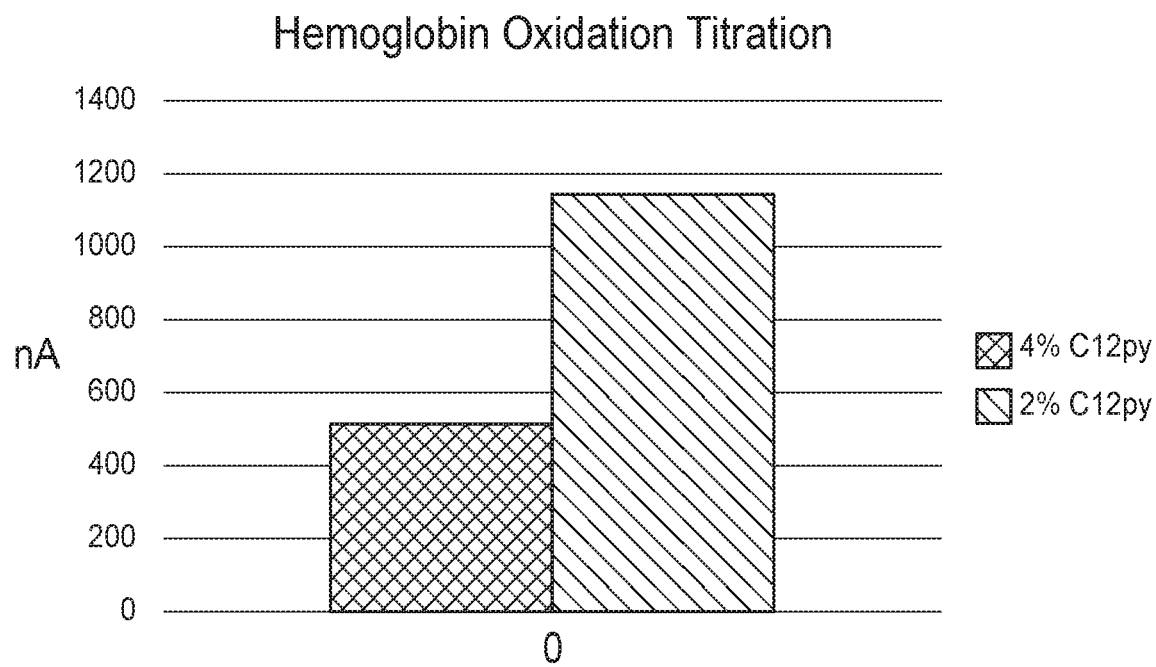
FIG. 1 shows a graph of the result of titration measurements of hemoglobin oxidation using 4% dodecylpyridinium chloride.

Certain terminology is used herein for convenience only and is not to be taken as a limitation on the embodiments of the systems and methods for sample preparation for enzymatic detection and quantification of HbA1c. The preparation techniques and the enzymatic detection and quantification techniques described herein enable electrochemical detection of HbA1c. In the drawings, the same reference letters are employed for designating the same elements throughout the several figures.

Hemoglobin A1c is formed when glucose binds to the N-terminal valine residue of the β-chains of hemoglobin. The percentage of HbA1c in total hemoglobin tells the tale of the last three months of average glucose measurements. It is an indicator of how well or how poorly a diabetic has controlled their diabetes and can also be an indicator of pre-diabetes.

Measuring HbA1c necessitates that hemoglobin and glycated hemoglobin are measured since HbA1c is measured as a percentage of total hemoglobin. Hemoglobin could can be measured electrochemically, since it is possible to react (with Fructosyl Amino acid oxidase as an enzyme or alternatively fructosyl peptide oxidase) Fructosyl-L-Valylhistidine (F-VH) electrochemically. This is merely an example of an electrochemical reaction scheme and many techniques described herein may be used with other electrochemical measurement schemes. Merely the electrochemical reaction of HbA1c is not enough to create a commercially viable assay. This is because a whole blood sample does not immediately provide for the availability of HbA1c to be measured. However, systems and methods to release the HbA1c may cause interference with various aspects of the assay.

Therefore, in order to provide a system that can function on whole blood, a number of techniques may be required to release HbA1c. In many embodiments, the steps involved in an enzymatic HbA1c assay include the following:

1. Lyse the red blood cells.
2. Oxidize the hemoglobin.
3. Allow protease to digest hemoglobin to release F-VH.
4. React F-VH with fructosyl peptide oxidase.
5. Measure reaction of F-VH.

As stated, related applications provide for how F-VH is reacted on an electrochemical test strip. The described testing mentioned here is tested with electrochemical sensors with reagent dried down to test F-VH. The experimental set-up for the testing described below consisted of adding whole blood to a reagent containing lysing reagents, oxidizing reagents or protease. This solution was then dosed onto the electrochemical sensor.

In many embodiments, the first step in providing an assay is to lyse the red blood cells. In many embodiments, lysing the RBCs can be done using a surfactant. Many surfactants may be available and some surfactants are better or more efficient at lysing RBCs. The surfactant may be non-ionic, anionic, cationic, or zwitterionic. Based on research and experimentation, in one embodiment a zwitterionic surfactant is used as it keeps the slightly denatured hemoglobin in solution. Other surfactants will lyse the cells, but n-Tetradecyl-N,N-dimethyl-3-ammonio-1-propanesulfonate (Zwittergent 3-14®) appears to keep the hemoglobin from falling out of solution and unable to react with the protease. This is an important characteristic of the surfactant. The chemical formula of Zwittergent 3-14 is $C_{19}H_{41}NO_3S$ and has a chemical name of n-Tetradecyl-N,N-dimethyl-3-ammonio-1-propanesulfonate. This characteristic may occur because n-Tetradecyl-N,N-dimethyl-3-ammonio-1-propanesulfonate (Zwittergent 3-14®) includes a strongly basic portion and a strongly acidic portion of the molecule of similar strength. This structure prevents irreversible binding of positively and negatively charged molecules. Since HbA1c is typically negatively charged it is thought that this property of n-Tetradecyl-N,N-dimethyl-3-ammonio-1-propanesulfonate (Zwittergent 3-14®) prevents binding of HbA1c to the surfactant. It is thought that other surfactants may be used that have similar characteristics to keep the slightly denatured hemoglobin in solution and characteristics that prevent the irreversible binding to the surfactant.

In many embodiments, the next step in the assay is to oxidize the hemoglobin. Oxidation of the hemoglobin is an important aspect of the assay. If the hemoglobin is not oxidized prior to coming in contact with the mediator, it will be oxidized by the mediator, creating an electrochemical response and unwanted background. Unfortunately many of the common substances that form methemoglobin are also electrochemically active. In one embodiment, by using a cationic surfactant and isothiazoline derivative, it is possible to oxidize the hemoglobin to form methemoglobin, in a way that will not electrochemically interfere. The cationic surfactant and isothiazoline derivative must be chosen in proper concentrations so that all hemoglobin is oxidized. The isothiazoline will not oxidize the hemoglobin fully on its own (FIG. 2), nor will the cationic surfactant completely oxidize the hemoglobin (FIG. 1). Without being held to a specific theory, both entities need to be present in proper concentrations to fully oxidize the hemoglobin (FIG. 3). In contrast to research done by previous parties, the absence of these two components does not provide for the full oxidation of hemoglobin. This is unrealized in previous research. Preferred examples are 1-Dodecyl pyridinium chloride as the cationic surfactant and 1,2 Benzisothiazol-3(2H)-one as the isothiazoline derivative.

FIG. 1 shows the result of titration measurements of hemoglobin oxidation using 4% dodecylpyridinium chloride which reduces electrochemical signal due to hemoglobin interference more than 2% dodecylpyridinium chloride in a 1:1 blood to reagent dilution. However, not all the hemoglobin was oxidized. It is desired for the background current to be less than 200 nA. A single blood sample was used at 60% hematocrit. In the various graphs shown herein, the y-axis provides for measured nano amperage (nA).

Figure 2:
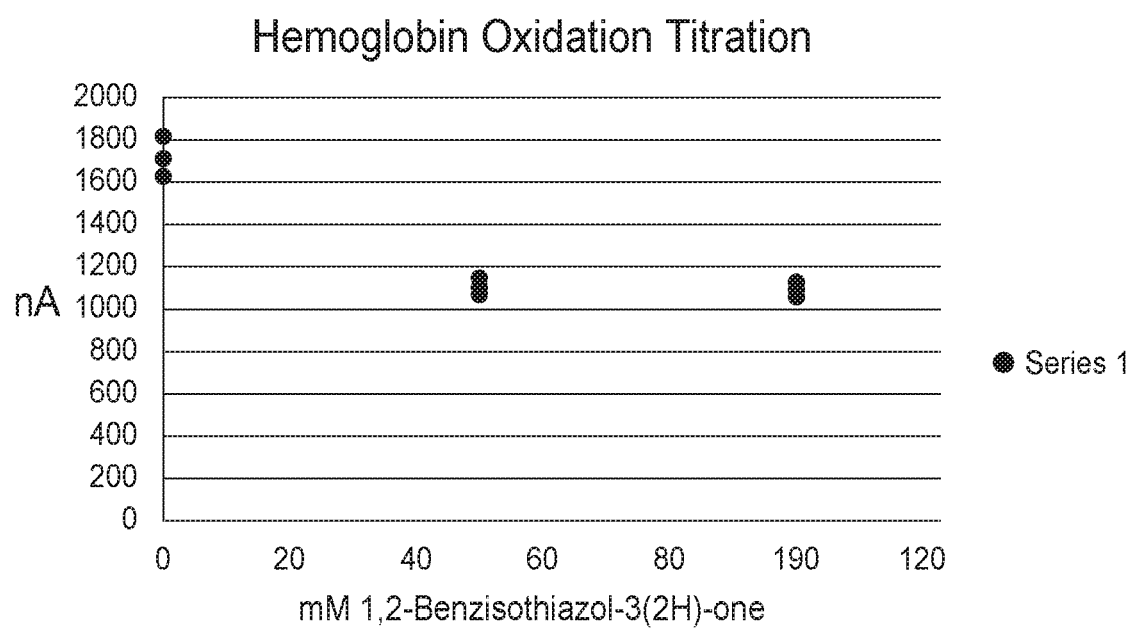
FIG. 2 shows a graph of the result of titration measurements of hemoglobin oxidation for by adding 1,2-Benzisothiazoline to lysed blood.
Figure 3:
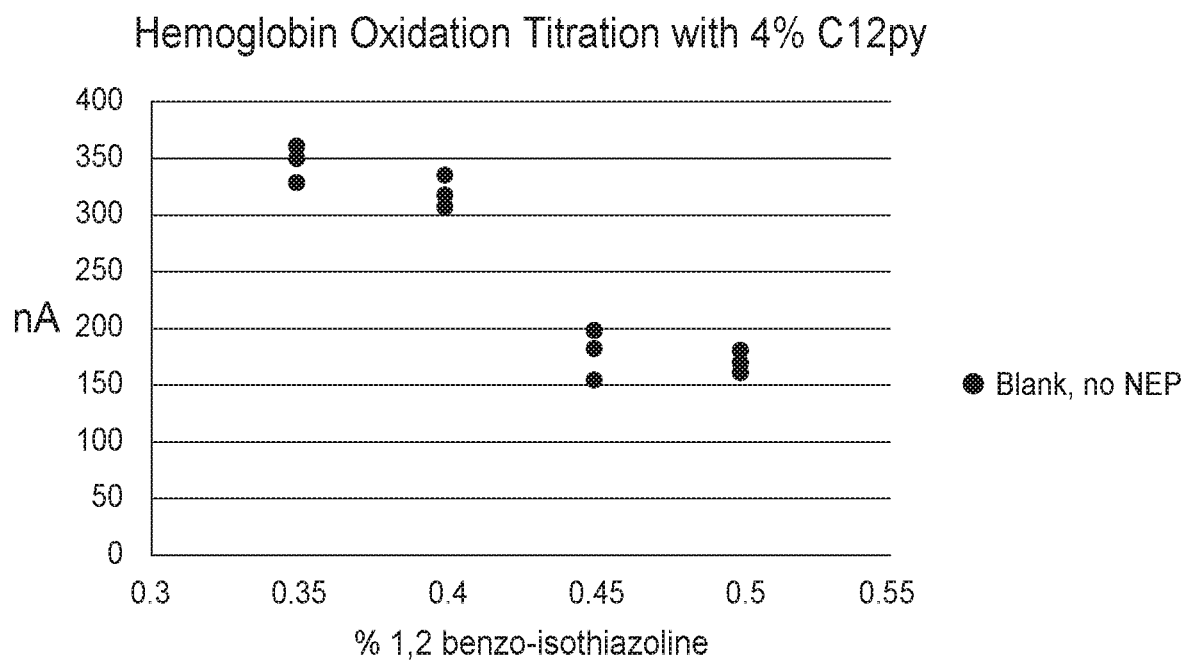
FIG. 3 shows a graph of the result of titration measurements of hemoglobin oxidation when using both dodecylpyridinium chloride and 1,2 benzisothiazoline.

FIG. 2 shows the result of titration measurements of hemoglobin oxidation for by adding 1,2-Benzisothiazoline to lysed blood. There was some hemoglobin oxidation, but not complete oxidation. Dilution factor was 1:1 blood to A1c reagent. A single blood sample was used at 60% hematocrit.

FIG. 3 shows the result of titration measurements of hemoglobin oxidation when using both dodecylpyridinium chloride and 1,2 benzisothiazoline. Hemoglobin is oxidized to methemoglobin. Dilution factor was 1:1 blood to A1c reagent. A single blood sample was used at 60% hematocrit. It is desired for the background current to be less than 200 nA.

In many embodiments, Protease Digestion is the next step in the process. The enzymatic path to measuring HbA1c begins with using a protease that is capable of degrading glycated hemoglobin selectively to a glycated hemoglobin degradation product. Neutral Proteinase is a choice protease for this reaction. Numerous neutral proteinases may be used in the reaction scheme as well as those produced by various bacterium. The reaction is seen below.

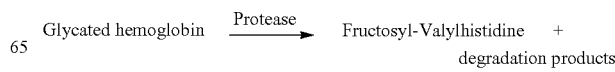

Neutral Proteinase is an extremely stable Zn-metalloendopeptidase that may be produced by the *Bacillus* species. In alternatives, it may be produced by *Paenibacillus polymyxa*.

Figure 4:
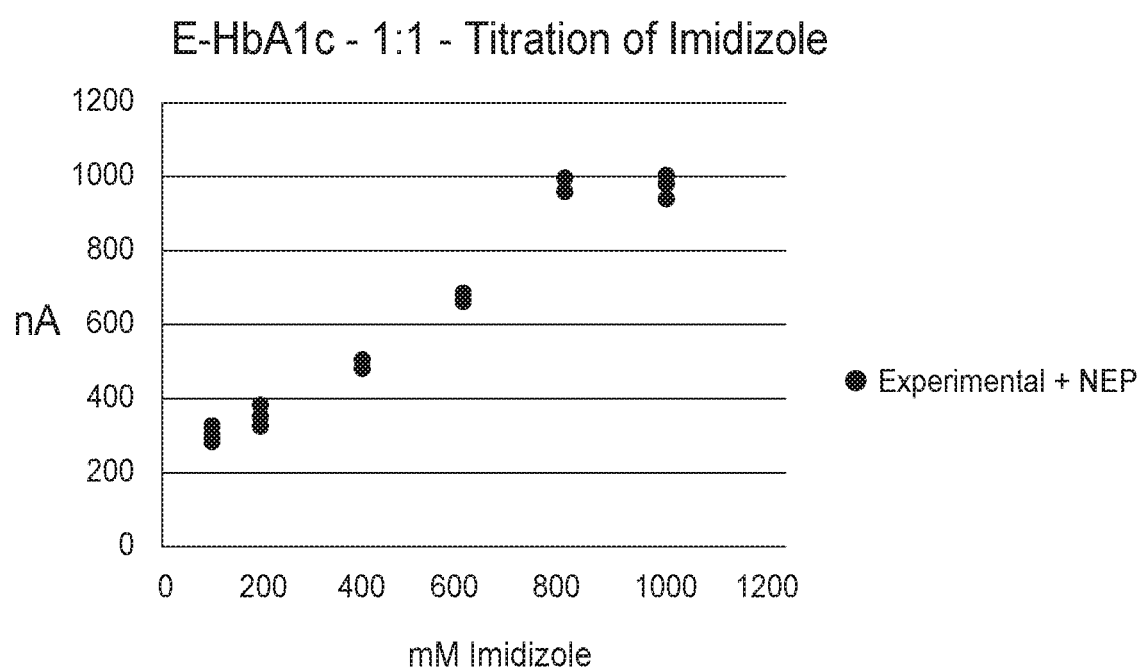
FIG. 4 shows a graph of the titration of Imidazole holding the pH at 7.5.

In order to optimize the digestion of the protease, the hemoglobin needs to be in a relaxed state and able to spread out. A relaxed state provides for the molecule to unfold. Commercial A1c assays for hospital analyzers have large dilution factors (e.g. 1 part blood to 100 parts reagent). In an electrochemical POC assay, the sample cannot be diluted that much and still have enough signal to read. The constraint of not being able to dilute the sample significantly posed a challenge to have the protease work efficiently. To overcome this challenge, in many embodiments imidazole is used as a ligand. Imidazole (C3H4N2) binds to the hemoglobin causing it to be in a relaxed state and thus allowing the protease to react more efficiently (FIG. 4). Other hemoglobin binding ligands such as sodium azide do not have the same effect as imidazole.

FIG. 4 shows Imidazole was titrated holding the pH at 7.5. At 1 M imidazole in the A1c reagent more protease digestion occurred releasing more F-VH. Dilution factor was 1 part blood (60% Hct) and 1 part A1c reagent. It is thought that various molarities of imidazole at various pHs may work. In some configurations, a concentration of the imidazole is picked between 0.5 to 2M. In some configurations, a pH of the imidazole is used between 6-8. One possible optimization of imidazole at its final concentration is at a 1:5 dilution is 760 mM. Various concentrations of imidazole or various analogs may be used. Lower concentrations in some cases may not sufficient enhance the activity of the protease for purposes of electrochemical assay that functions in the proper volumes and time periods for point of care uses and salability. The sale holds true for pH, as extreme pH levels may upset other aspects of the assay.

In various alternatives, other analogs of imidazole may be used. Analogs may include Benzimidazole, Dihydroimidazole, Pyrrole, Oxazole, Thiazole, Pyrazole, Triazoles, Tetrazole, Pentazole, Furazan, Isothiazole, Thiazole, Thiadiazole, and various other Azoles. Additionally, molecules having imidazole as a side chain such as histidine or other molecules having imidazole or a imidazole analog as a side chain may be used in place of imidazole in various alternatives, may enhance the protease.

Figure 5:
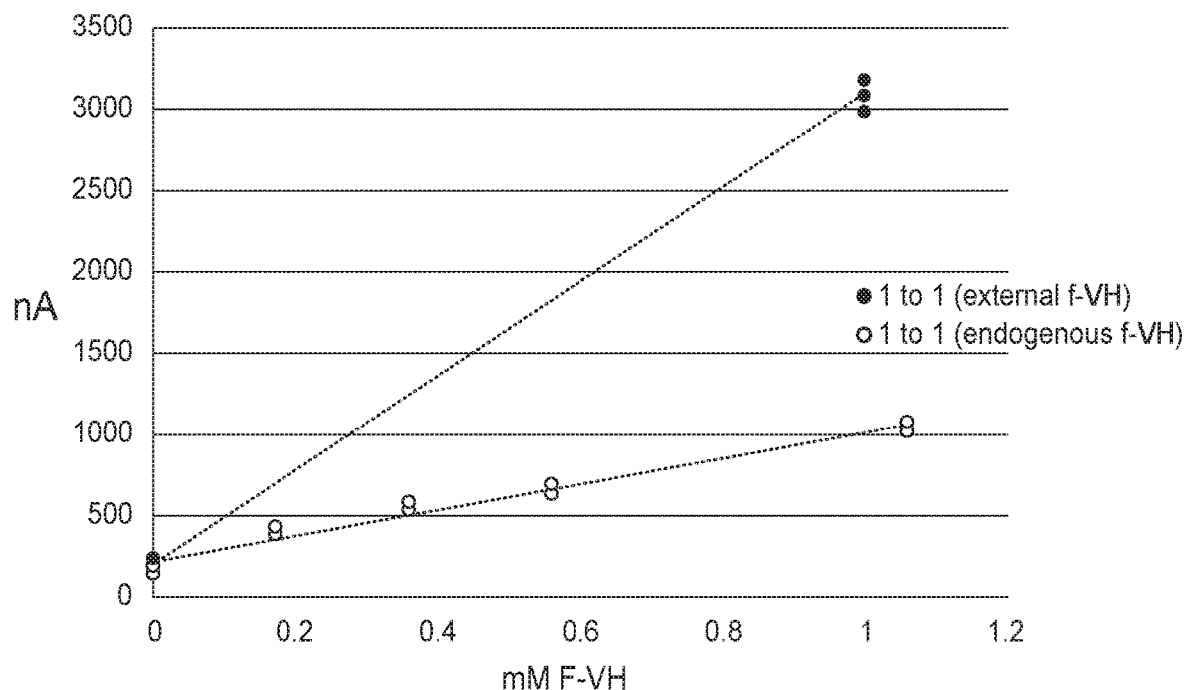
FIG. 5 shows a graph of a dose response graph with different levels of imidazole.
Figure 6:
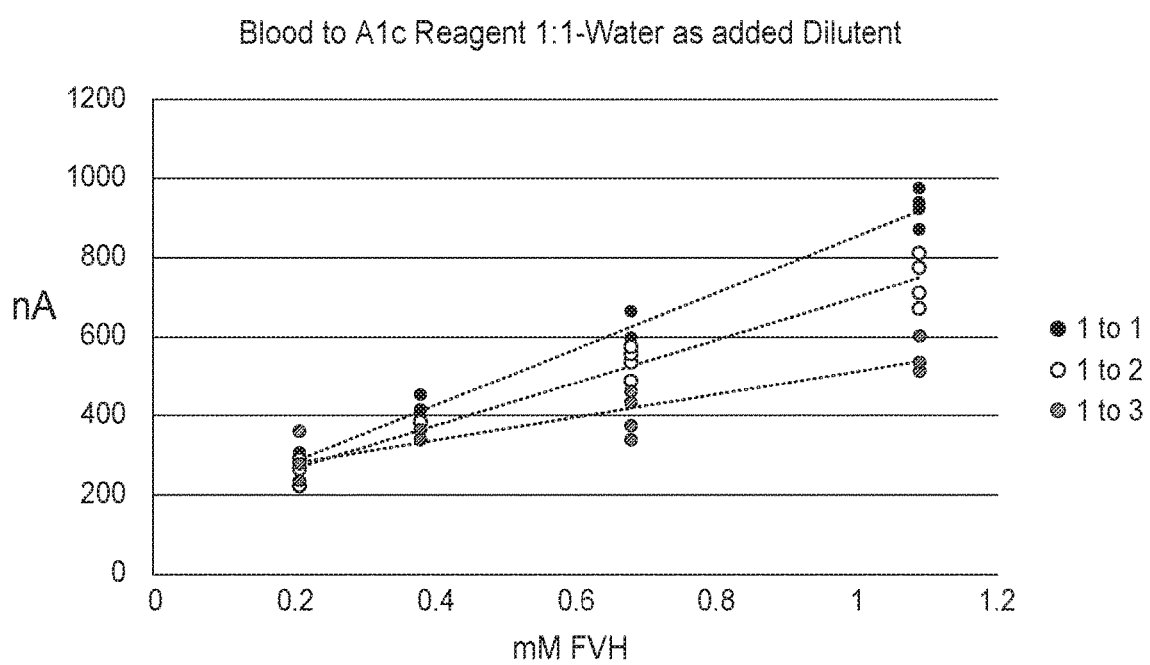
FIG. 6 shows a graph of how blood donors were used to measure endogenous F-VH.

Imidazole, while it enhances the ability of the protease, will not allow for complete digestion by itself in minimally diluted solutions. There needs to be some space for the unfolding of the hemoglobin. Initially, in one embodiment, a development model used a 1:1 dilution of whole blood to reagent with hopes of drying down the reagent on a strip. By using large concentrations of imidazole, protease efficiency was increased (FIG. 4), but complete digestion was not possible (see FIG. 5). Believing that more space was required for hemoglobin unfolding, water was added as a diluent and tested dilutions of 1:2 and 1:3. This testing showed a proportional decrease in signal (FIG. 6). Just adding more space for the hemoglobin was not enough for the protease to work. FIG. 5 shows that even with additional imidazole in the reagent, the assay was unable to match to theoretical dose response using external F-VH. FIG. 6 shows how blood donors were used to measure endogenous F-VH. The ratio of blood to A1c reagent (lysing/protease) was 1:1 with water added as extra diluent.

Figure 7:
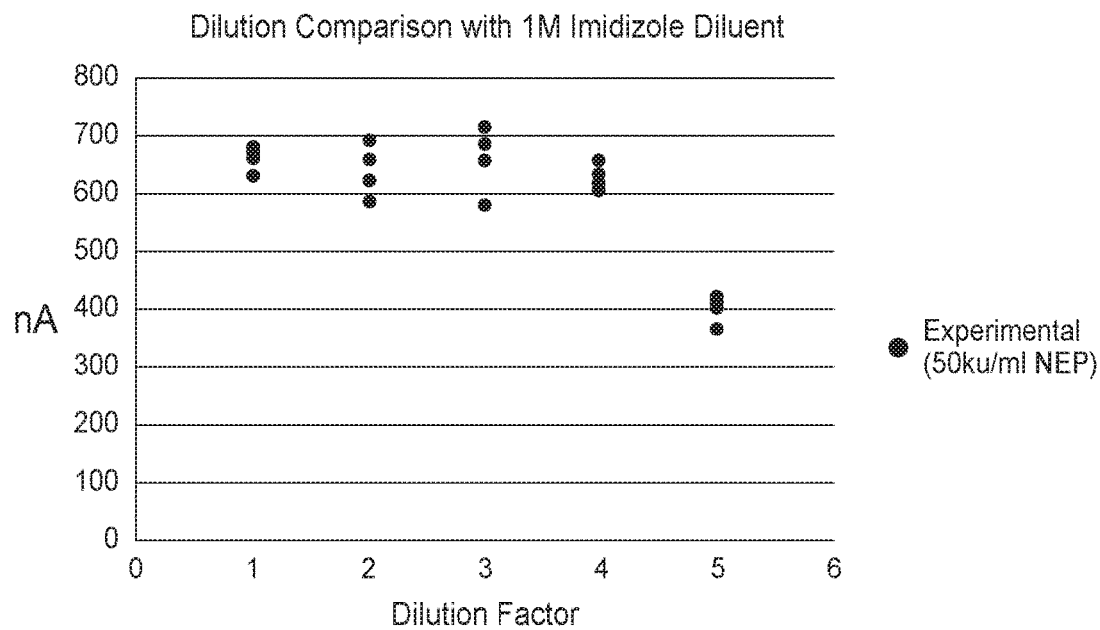
FIG. 7 shows a graph of dilution comparison using 1 M imidazole as the diluent.

Using water as a diluent to create space for the hemoglobin to unfold did not show more protease digestion. However, when a 1 M solution of imidazole was used as the diluent, the same signal was observed for 1:1, 1:2, 1:3, and 1:4 dilutions (FIG. 7). It was only at a 1:5 dilution where the electrochemical signal decreased. This experiment confirmed that protease efficiency is determined by both space (room for hemoglobin to unfold) and imidazole (putting hemoglobin in relaxed state).

FIG. 7 shows dilution comparison using 1 M imidazole as the diluent, pH 7.5; the electrochemical signal did not decrease until the 1:5 dilution.

Therefore, based on these experimental results a system for determining HbA1c can be created. In many embodiments, a system for obtaining an electrochemical enzymatic HbA1c assay includes many aspects described above. In one embodiment, by using an oxidizing system that does not interfere electrochemically, it is possible to react with hemoglobin to form methemoglobin. This is important so that the mediator does not react with hemoglobin. The surfactant n-Tetradecyl-N,N-dimethyl-3-ammonio-1-propanesulfonate (Zwittergent 3-14®) was chosen to lyse the cells and keep the slightly denatured hemoglobin in solution. Using large concentrations imidazole with a small dilution (1:5) allows for the protease to efficiently release all the F-VH. Both space (dilution) and imidazole are required for optimal protease function.

Figure 8:
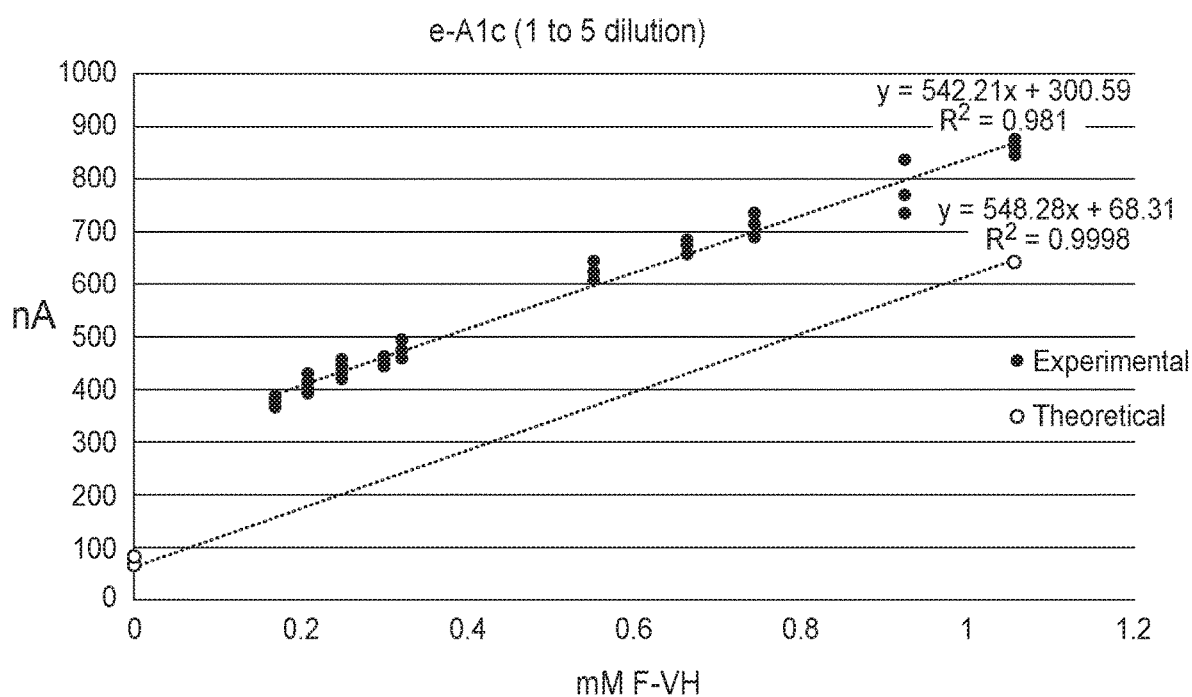
FIG. 8 shows a graph of levels of hypothetical hemoglobin represented Fructosyl-L-Valylhistidine compared to the amperage of the electrochemical tester.

FIG. 8 illustrates proof of concept of the systems described (Endogenous F-VH reaction). Whole blood was mixed in a 1:5 dilution with a reagent containing the lysing surfactant, oxidizing agents, imidazole buffer and protease. The blood samples consist of five samples which were altered to obtain 20% and 60% hematocrit. An excellent correlation was obtained with a slope equivalent to the theoretical reaction of external F-VH at a 1:5 dilution. As can be seen the R-squared value is approximately 0.981.

In one embodiment, a strip design includes many of these techniques. The amount of glycated hemoglobin in any sample is typically very small. The sample is additionally diluted to enable the oxidation and detection of the HbA1c. In order to accommodate the small amount of detectable HbA1c, interdigitated electrodes are used to enhance the electrochemical signal. The oxidizing agents and protease are dried down on a runway/channel to be reconstituted by the blood solution. A sampler is used to collect the blood and mix it with a lysing/imidazole solution before the solution is deposited on the electrochemical test strip. FIG. 9 shows one embodiment of an electrochemical strip for HbA1c.

Strip 910 includes a sample deposit area 915. In usage, a sampler/mixer collects a sample from a user. The sample is then mixed with a lysing/imidazole solution, according to the above described configurations. Then the sampler/mixer is then use to dose the mixed sample to sample deposit area 915. The strip 910 includes a first and second track 920, 925. In the transport channel section 930 of both tracks 920, 925 of the strip 910, oxidation and digestion of Hb occurs. Transport channel section 930 may be tube or other channel designed to flow the sample to the interdigitated electrodes 940. This channel may be vented to enhance the flow of the sample. This channel is optionally heated to enhance digestion activity. The heating may be applied by the meter associated with the strip 910. The strip 910 may include heating elements that may be powered and activated by the meter, or the meter may include the heating elements. Temperature sensors may be included in the strip 910 or the associated meter to regulate the temperature level. The interdigitated electrodes 940 are shown at the end of the strip 910 as our contacts 950 which are used by a corresponding meter in order to measure the electrical activity of the strip 910. In alternative embodiments, the transport channel section may be omitted and the oxidizing agents and protease may be added in a sampler/mixer. In some embodiments, the sample/mixer may include 2 or more compartments for various portions of the mixing process.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for preparing a sample containing hemoglobin HbA1c for measurement by an electrochemical sensor, the system comprising:
   a lysing mixture, the lysing mixture including a zwitterionic surfactant;
   an oxidizing mixture, the oxidizing mixture including a cationic surfactant and an isothiazoline derivative; and
   a protease mixture, the protease mixture including a molecule including an azole, wherein the system includes a sampler/mixer device, and the lysing mixture is located in the sampler/mixer device, wherein the sampler/mixer device is configured to dose a sample area of a test strip, wherein the zwitterionic surfactant is n-Tetradecyl-N,N-dimethyl-3-ammonio-1-propanesulfonate (Zwittergent 3-14®) and the cationic surfactant is 1-Dodecyl pyridinium chloride and the isothiazoline derivative is 1,2 Benzisothiazol-3(2H)-one and at a 1:5 dilution.

2. The system of claim 1, wherein the protease mixture includes Neutral Proteinase.

3. The system of claim 2, wherein the azole is imidazole.

4. The system of claim 3, wherein the imidazole is in a range of 0.5 M to 2 M and at a pH of 6-8.

5. The system of claim 4, wherein the system includes a test strip and the oxidizing mixture and protease mixture are located in the test strip.

6. The system of claim 1, wherein the sampler/mixer device is separate from the test strip.

* * * * *